United States Patent [19]
Allen

[11] Patent Number: 5,315,375
[45] Date of Patent: May 24, 1994

[54] SENSITIVE LIGHT DETECTION SYSTEM
[75] Inventor: Fritz S. Allen, Corrales, N. Mex.
[73] Assignee: Acrogen, Inc., Oakland, Calif.
[21] Appl. No.: 833,926
[22] Filed: Feb. 11, 1992
[51] Int. Cl.[5] .......................................... G01N 21/64
[52] U.S. Cl. .................................. 356/417; 250/461.2
[58] Field of Search ............................... 356/318, 417; 250/458.1, 459.1, 461.1, 461.2

[56] References Cited
U.S. PATENT DOCUMENTS

| | | | |
|---|---|---|---|
| 4,293,225 | 10/1981 | Wheaton et al. | 356/417 |
| 4,410,271 | 10/1983 | Matthews | 356/318 X |
| 4,689,652 | 8/1987 | Shimada et al. | 357/30 |
| 4,755,921 | 7/1988 | Nelson | 362/307 |
| 5,026,159 | 6/1991 | Allen et al. | 356/318 |
| 5,032,730 | 7/1991 | Iwasaki | 250/461.2 |
| 5,108,179 | 4/1992 | Myers | 356/318 X |

OTHER PUBLICATIONS

C. Jacobsen, et al. (1987) Phys. Med. Biol. 32:431–437. Quantitative imaging and microanalysis with a scanning soft x-ray microscope.
G. Renault, et al. (1983) J. Biomed. Engineering 5:243–247. Cancelling of fresnel reflations in in situ double beam laser, fluorimetry using a single optical fibre.

*Primary Examiner*—Vincent P. McGraw
*Assistant Examiner*—K. P. Hantis
*Attorney, Agent, or Firm*—Bertram I. Rowland

[57] ABSTRACT

Apparatus and method for using the apparatus are provided, where the apparatus provides for a light beam of variable area in a narrow wavelength band, where the size of the beam incident on a sample and relative movement of the sample and light irradiation and collection means is carefully controlled, so as to vary the site of interrogation. A discrete element collector system is used to efficiently collect the emitted light from the sample and direct it to a focusing lens, filter pack and photodetector for collection of the light and transmitting signals to electronic circuitry for analysis.

21 Claims, 5 Drawing Sheets

SENSITIVE LIGHT DETECTION SYSTEM

INTRODUCTION

1. Technical Field

The technical field of this invention is light detection instrumentation and methods.

2. Background

The need to detect and quantitate light occurs in a large variety of situations. One application of this need is the detection of analytes for the determination of the presence or amount of a particular analyte. In many assays for analytes, one is concerned with either absorption or emission (e.g., fluorescence) of light. In both situations, one irradiates a sample with light and then attempts to detect the effect of the sample on the transmitted or emitted light. In the case of emitted light, non-analyte molecules may also emit light resulting in a relatively large background noise, which results in the introduction of substantial error in the measurement of the effect of the sample on the light. There are also additional systematic errors which further add to the uncertainty of the result.

There have been numerous efforts to develop instrumentation which would allow for the detection of very low signal levels. As the detection or quantitation of an analyte occurs at ever reduced levels, the need for such instrumentation becomes increasingly significant. In developing such instrumentation, a number of factors become important. The instrumentation should maximize sensitivity to an analyte-specific signal. In order to achieve maximum sensitivity, the instrument design must recognize sources of extraneous signal (noise) and minimize them. In addition, the instrumentation must be relatively economic, so as to be able to find wide application. Also, desirably the various components of the instrumentation should be relatively easily reproducible and maintain their characteristics over long periods of time, so that one can avoid frequent calibration. Other considerations include ease of manufacture and operation and good performance.

Relevant Literature

Jacobsen et al., Phys. Med. Biol. (1987) 32:431–437 describe quantitative imaging and microanalysis with a scanning soft x-ray microscope. Renault et al., J. Biomed. Eng. (1983) 5:243–247 describe the canceling of Fresnel reflections in situ, double beam laser, fluorimetry using a single optical fiber. U.S. Pat. No. 4,689,652 describes an integrated optical image sensor with transparent substrate which has an incident light from a source focused through a substrate onto a document for reflection onto a photosensor via a Fresnel lens array. U.S. Pat. No. 4,755,921 describes a catadiaoptric lens which finds use in this invention.

SUMMARY OF THE INVENTION

Detection and quantitation of light from a fluorescent signal is obtained by controlling the size and intensity of a laser beam incident on a stage, where the size and location of the beam may be varied. The emitted fluorescent light is collected with optionally, a reflector, and a discrete element collector system and directed to a photodetector system for detection and analysis. Fluorescence intensity and position can be analyzed in relation to extremely low amounts of analyte.

DESCRIPTION OF THE SPECIFIC EMBODIMENTS

Figure 1:
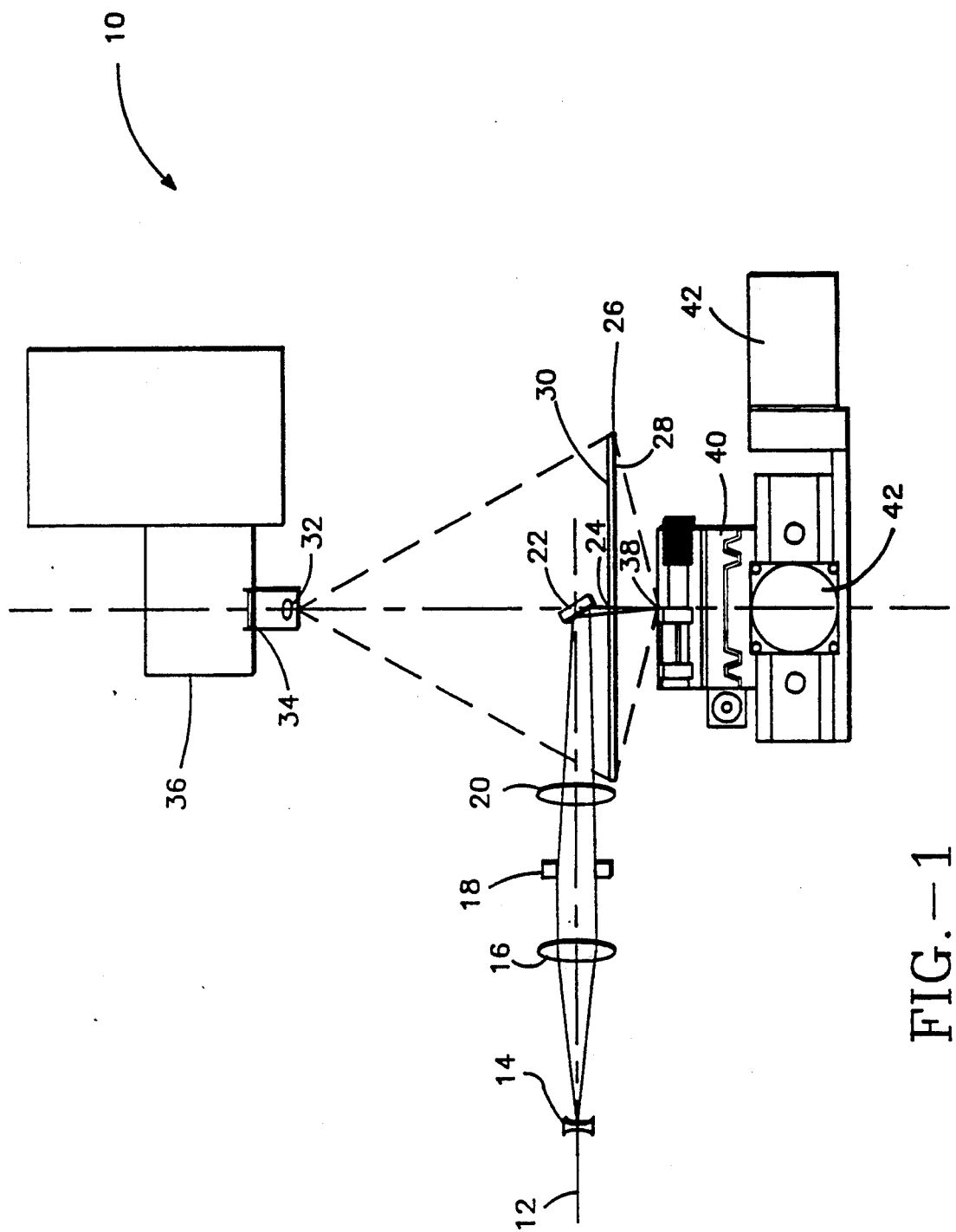
FIG. 1 is a diagrammatic elevational view of one embodiment of the subject apparatus.

Apparatus and methods are provided for detecting low levels of emitted light, where the emitted light may be related to the amount of analyte in a sample. Particularly, collimated light of a narrow wavelength range is directed onto the sample, where the area exposed to the incident beam may be varied. The emitted light is then collected with a discrete element collector system and directed to a photodetector for quantitation and analysis.

A discrete element collector is an array of discrete optical elements arranged to refract or reflect light from the sample point into a quasi-collimated beam. An example of such a collector is a low f-number Fresnel lens/reflector array of the type produced by 3M Corporation (Minneapolis, Minn.).

The apparatus can be used for detecting a wide variety of analytes employing a variety of protocols, where emitted light is the detected signal. Emitted light may be as a result of fluorescence, chemiluminescence, phosphorescence, and the like. The sample may be a fluid sample or a solid sample. Conveniently, the detected label may be bound non-diffusively to a support, where controlled distribution of the label in relation to the amount and/or nature of the analyte is provided. Therefore, one may provide for homogeneous or heterogeneous assays, where the detectable label may be in solution or bound to a surface. In addition, assays may be competitive or complementary as to the relationship of the conjugate employing the detectable label and the analyte.

Desirably, the assays will involve a particle fluorescent label, where the number of particle labels bound to a surface is in relation to the amount of analyte. The assays will normally involve specific binding pairs, where by specific binding pairs it is intended that a molecule has a complementary molecule, where the binding of the members of the specific binding pair is at a substantially higher affinity than random complex formation. Thus, specific binding pairs may involve haptens and antigens (referred to as "ligands") and complementary binding members, such as antibodies, enzymes, surface membrane protein receptors, lectins, etc. (generally known as "receptors") and nucleic acid sequences, both naturally occurring and synthetic, either RNA or DNA, where for convenience nucleic acids will be included within the concept of specific binding members comprising ligands and receptors.

In carrying out the assay, there will normally be involved a conjugate of a specific binding member and a detectable label. As already indicated, a fluorescent label will be preferred, but other labels which may be detected include chemiluminescent labels, enzyme labels which provide for a fluorescent product or chemiluminescence, or other label which provides for emitted light. Methods of preparing these conjugates are well known in the literature. Depending upon the analyte, various protocols may be employed, which may be associated with commercially available reagents or such reagents which may be modified.

Assays which may be performed include ELISA, EMIT, SLFIA, sandwich assays, and the like.

Of particular interest is the detection of specific sequences of nucleic acids. The sequences may be detected by employing probes which are labeled to provide for a detectable signal. Thus, the probes may be labeled with fluorescent molecules or alternatively with a molecule which will allow for binding to a fluorescent molecule conjugate, e.g. biotin, with a fluorescent-conjugated strept/avidin. Thus, by binding the nucleic acid sample to a surface, the binding of a probe having an homologous sequence under appropriate complex formation conditions will indicate whether the particular sequence is present in the sample. Alternatively, one may use intercalating dyes, where the dye will only intercalate double-stranded nucleic acid and will provide for a fluorescent signal. Numerous variations exist in performing assays for detecting a specific sequence, which techniques may be employed here, so long as there is an emitted light signal. The analyte may be a single molecule or an aggregation, such as a virus or cell.

The assay medium will have low concentrations of analyte, generally at picomolar or less, frequently femtomolar or less. Assay volumes will usually be less than about 100 $\mu$l, frequently less than 10 $\mu$l and may be 1 $\mu$l or less. The cross-sectioned area of the sample to be irradiated will generally be not greater than 100 mm$^2$, usually not greater than about 50 mm$^2$ and may be as low as 0.1 mm$^2$. The area to be measured will depend on the concentration of the analyte, the size of the individual site to be irradiated, the ease with which individual signal units may be discriminated, and the like.

In order to measure the signal, a device is employed which allows for the detection of very low levels of emitted light. For the most part, the device will be employed with a fluorescent signal, so that the device will provide for the radiation of the sample with collimated light of narrow wavelength range. In addition, the methodology which is preferred is described in application Ser. No. 354,137, now U.S. Pat. No. 5,026,159. In this methodology, two measurements are made, where the irradiated sample is different, but the incident light intensity is the same. This can be as a result of using irradiation beams of different diameter or beams of the same diameter at different sites or combinations thereof.

For the most part, the light source will be a laser, where the intensity of the beam may vary from a power rating of 1 $\mu$W to about 20 mW. The light wavelength may be varied widely, depending upon the absorption characteristics of the fluorescent label. For the most part, the light will be at a wavelength above 350 nm, usually above 400 nm, and usually below 700 nm, more usually below about 550 nm. Desirably, the fluorescer will provide for a large Stokes shift, usually at least about 20 nm, preferably at least about 50 nm.

For varying the beam size, one may use a movable lens, which by varying the distance from the sample will change the beam size. By employing appropriate stepper motors, one can provide for smaller or greater changes in the beam with each step. In addition, the sample may be mounted on a movable stage, where the stage allows for movement in both the X and Y direction, so that various sites in the sample may be interrogated. Alternatively the light irradiating system may be movable in relation to the sample to interrogate various sites.

The light which is emitted from the sample is then efficiently collected using a discrete element collector system which provides for the collection of the light and its transmission to a photodetector. The discrete element collector system will usually be a multi-lens system, where the collector lens, proximal to the sample, will generally have a low f-number, usually less than about 2 and greater than about 0.05, generally being in the range of about 0.075 to 1.0. The low f-number discrete element collectors do not normally produce a high quality collimated beam but the resolution of the system is primarily determined by the size of the beam interrogating the sample, and not by the quality of the low f-number light collection optics. Therefore, optics of very high quality are not necessary for the discrete element collectors. However, by employing a second lens of about the same diameter and a larger f-number, usually greater than 0.5, generally from about 1 to 10, the light may be focused on the detector. The discrete element collector lens and the second lens, will generally have a separation of from about 0 to 50 cm, usually being in close proximity of from about 0.1 to 5 cm. The discrete element collector lens will usually be at least about 1 cm$^2$ and may be as large as about 1×10$^4$ cm$^2$, usually not greater than about 500 cm$^2$ in area.

By including a perfect spherical reflector behind the emitter to reflect the light going away from the detector back through the source and into the discrete element collector system, the fraction of solid angle collected into the collimated beam emergent from the discrete element collector system can be doubled. The spherical reflector must be placed one sphere radius away from the source and on the opposite side of the emitter from the discrete element collector. For emission samples which have a finite size, S, the spherical reflector radius should be on the order of 10 times S, or greater, in order to cause the source to remain point-like relative to the reflector. If this is not the case, larger portions of the light will not be reflected back into the lens.

The solid angle of light which will be collected can be calculated based on the collection system employed.

By using the above system the solid angle fraction collected in a system with an ideal collector can be as high as 0.90, while more realistically with f-numbers for the discrete element collector varying from 0.5 to 0.05, estimated solid angle fractions will be in the range of about 0.26 to 0.81.

Electronics are used for analyzing the signal from the sample, which can then be related to the presence or quantitation of an analyte.

For further understanding of the invention, the figures will now be considered.

In FIG. 1, the apparatus 10 has a laser beam 12 which is passed through a first lens 14 which expands the laser beam and directs the beam to second lens 16 where the beam is recollimated. The collimated beam is then passed through an adjustable aperture 18 to define the diameter of the beam and finally through focusing lens 20. Focusing lens 20 is mounted on a stage, not shown, where focusing lens 20 may be moved along the optical axis, so as to change the beam diameter as it is incident on the sample. The laser beam 12 exits the focusing lens 20 and is reflected by a first surface mirror 22. The light then passes through a hole 24 in discrete element collection system 26, which comprises a first discrete element collector lens 28, such as a catadioptric array, for collecting the emitted light and a second discrete element collector lens 30 for focusing the light. Usually, the focal length of the first discrete element collector or catadioptric array lens, which will have a structure analogous to a Fresnel lens, will be substantially less than the focal length of the second lens (which may or may not be a Fresnel lens), generally being less than about 60% of the focal length of the second lens. The collection half-angle for the first discrete element collector lens will usually be at least about 45° for direct emission. The emitted focused light will then be transmitted to a second lens 32 and directed to a filter pack 34, which serves to exclude light outside of the wavelength range of the light emitted from the fluorescer. The light of the desired wavelength is then detected by a photomultiplier tube and preamplifier 36 for transmission to electronic circuitry for analysis.

The sample 38 is supported by X-Y stage 40, which allows for micropositioning of the sample in relation to the incident light. Stepper motor 42 are provided for accurate movement of the sample 38 in the X and Y direction.

Figure 2:
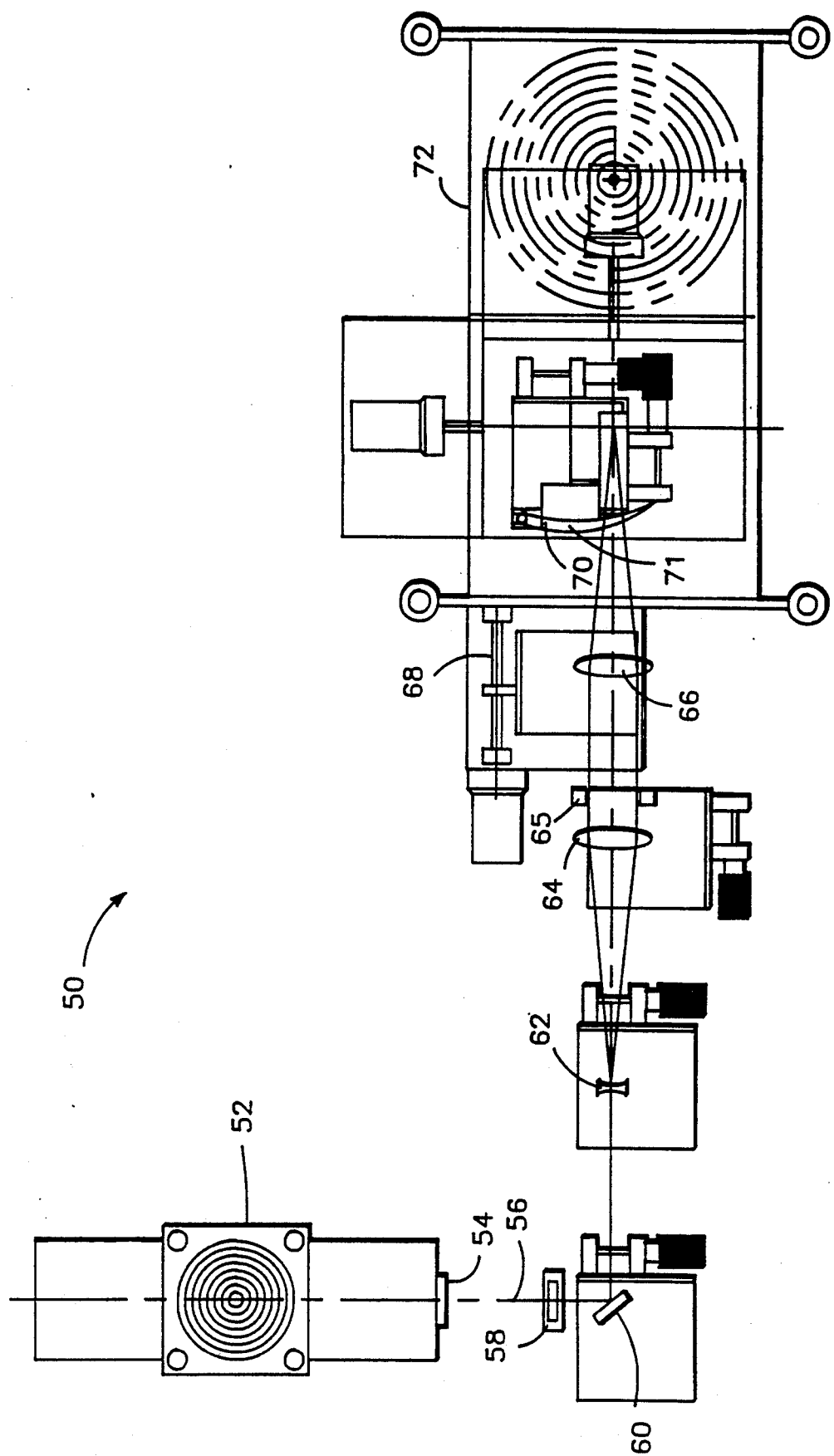
FIG. 2 is a diagrammatic plan view of the embodiment according to FIG. 1.

In FIG. 2, the device 50 is shown diagrammatically with a laser source 52 fitted with beam shutter 54. The laser beam 56 is directed through a line filter 58 and then is reflected by turning mirror 60 into the lens system comprising an expanding lens 62, a collimating lens 64, an adjustable aperture 65, and a focusing lens 66 which is mounted on a stepper driven stage 68. A sample stepper stage 70 is provided to support and move the sample, holding the sample in place with slide holder 71, which sample is positioned under moveable discrete element collector system 72 (shown displaced from operational position directly above the sample).

Figure 3:
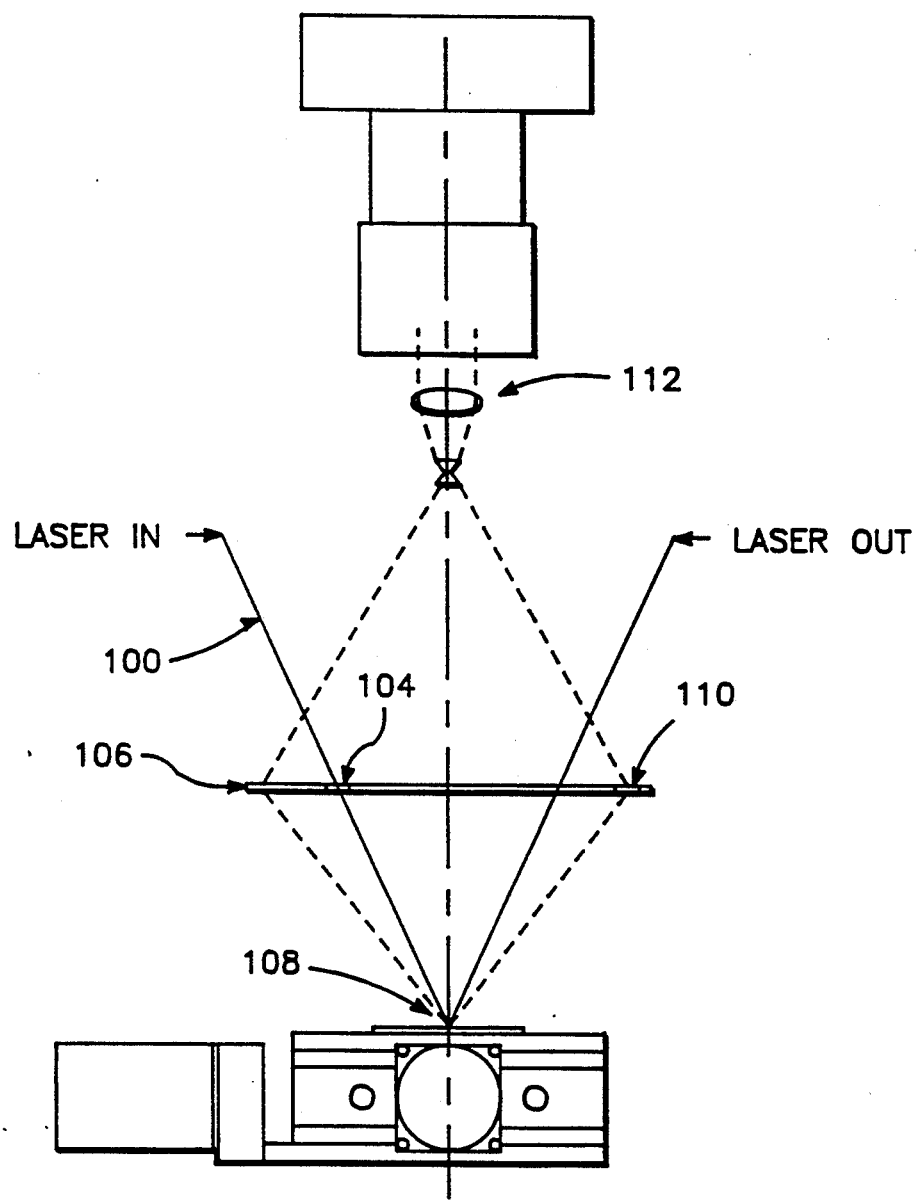
FIG. 3 is a diagrammatic elevational view of an alternative embodiment of the subject invention.

In an alternative embodiment, FIG. 3, instead of having the light incident to the sample being at right angles to the sample, the incident light is at other than normal to the sample. In FIG. 3, a laser beam 100, which has been processed as described in FIG. 1, is reflected by reflecting mirror (not shown) so as to pass through hole 104 in discrete element collector system 106. The light strikes the sample 108 and is reflected from the sample through hole 110 and then discarded by any convenient means. The emitted light from the sample 108 is focused by discrete element collector system 106 and directed to lens 112 to be processed as previously described in FIG. 1.

Figure 4:
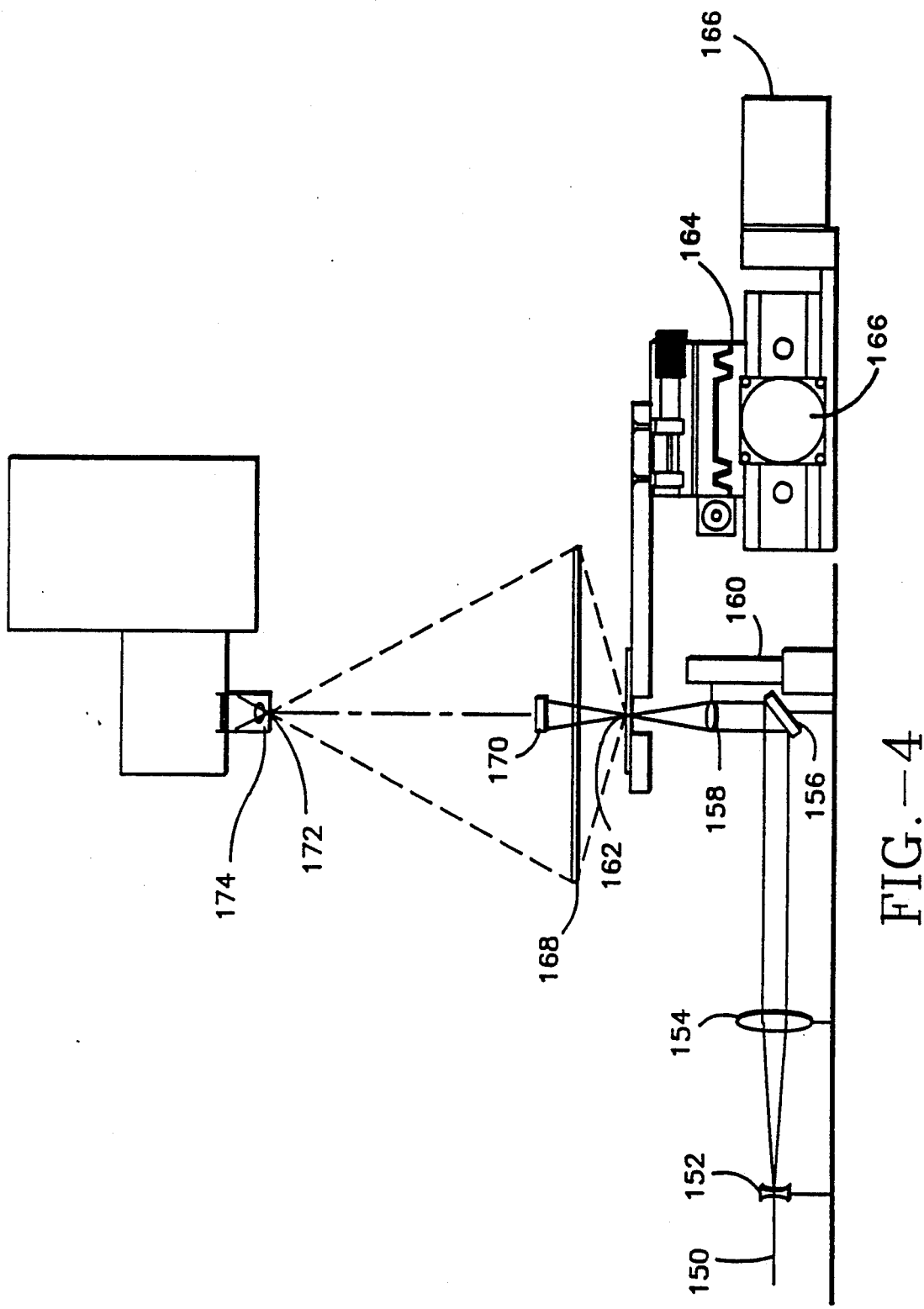
FIG. 4 is a diagrammatic elevational view of a second alternative embodiment of the subject invention.

In a second alternative embodiment, FIG. 4, instead of having the light incident to the sample originating above the sample and passing through holes in the discrete element collector system, the sample is mounted on a transparent substrate and the incident light strikes the sample from below. In FIG. 4, a laser beam 150 is expanded through a first lens 152, which expands the laser beam and directs it to a second lens 154 where the beam is recollimated. The collimated beam is reflected by a first surface mirror 156 and directed to a focusing lens 158 mounted on an adjustable stage 160 which allows the beam to be focussed at the sample plane. The sample 162 is supported by X-Y stage 16 which allows for micropositioning of the sample in relation to the incident light. A stepper motor 166 is provided for accurate movement of the sample 16 in the X and Y direction.

Unabsorbed excitation light passes through the discrete element collector system 168 and is absorbed by the long pass filter 170. Alternatively, the long pass filter may be replaced by a dichroic mirror placed at a 45° angle to the unabsorbed incident beam and reflecting the beam away from the detector where it can be discarded by any convenient means.

The emitted light from the sample 162 is focussed by the discrete element collector system 168 and directed through spatial aperture 172 and to collector lens 174 to be processed as previously described in FIG. 1.

Particular embodiments have been developed as follows.

The major components that make up the instrument are:
Laser and Optics
Electronics
Computer
Software
Mechanical assemblies.

Laser and Optics

A Spectra Physics Model 161C argon ion laser and a Model 261C power supply is used to generate the light source for the measurements. The laser delivers up to 20 mWatt of polarized, pure 488 nm, multimode optical output. The power supply requires 110 V, 60 Hz, at 15 Amp and connects to the laser head. A remote control unit connects to the laser power supply to provide a keyed interlock, power level adjustments, a power level readout, and interlock status information. This same connector permits control by way of computer operation. The computer controls the laser by opening and closing a shutter window at the head of the laser. When the shutter is open, a 0.65 mm beam of about 1.5 mrad divergence is aimed into a ¼ inch hole of the instrument enclosure and delivered to the optical portion of the system.

The first component in the optical path of the beam is a 488 nm band pass laser line filter. This filters out unwanted light from reaching the next component, the steering mirror. A 1 inch diameter first surface mirror directs the beam down the optical axis. The components along this axis transform and deliver selected beam sizes to the sample lying on the X-Y stage. The first element on the optical axis, a bi-concave lens with a diameter of 12.7 mm and a focal length of −12.5 mm, expands the laser beam. A bi-convex lens of diameter 50.8 mm and focal length of 200 mm is located 187.5 mm down line and re-collimates the beam at a diameter of about 25 mm. The specifications of these lenses would account for an expansion to only 9.75 mm but, the initial divergence of the beam, coupled with about 120 cm of distance to the expanding lens, accounts for the larger diameter.

The re-collimated beam is clamped to a fixed 20 mm beam using an adjustable aperture. This 20 mm beam is then delivered to the final focusing lens having a 233 mm focal length. The lens is mounted on a motor driven translation stage that permits changing the beam size that is incident upon the sample by moving the lens with relation to the sample. Moving the lens back and forth (the Z axis) then varies the beam diameter on the sample. The beam is next bounced off of another first surface mirror and directed through a hole in the discrete element collector system, a combination of a discrete element collector and a focusing lens and delivered to the sample.

Newport model 420-1 translation stages permit fine tuning of all the lenses and mirrors.

All of the optical components are mounted on an SE series Newport steel core breadboard table. The table is 3×4 ft, 2 inch thick with a precision formed steel honeycomb core. Holes are spaced on 1 inch centers for ease of mounting. This table also holds the PMT detector and has holes for the control cables to the electronics of the instrument. The table provides the area for placement of the X-Y stage, the laser components, the control electronics, and power supplies.

Some light scattering occurs at each mirror and lens in the optical path and from air contaminants that the beam passes through. The light from these sources has been shielded from the PMT detector by use of black painted cardboard pieces and black optical tape. This shield is also provided as an enclosure for the optical elements to minimize dust collection. The emergent beam is virtually all that exits from the shield.

The light emitted from the sample is collected by an 8 inch discrete element collector (SCOTCHLENS, direct lens, 3M, Minneapolis, Minn.) with an effective focal length of 1.0 inch. This gives the instrument a collection angle of 152 degrees for direct emissions. The light captured and collimated by this collector is focused by an 8 inch Fresnel lens with a focal length of 7.0 inch. This second lens is mounted directly on top of the first and a hole is drilled through the center of both for the incident light beam. The final bending mirror for the incident optics is mounted on a T-rail directly above the hole. Only a very small portion of the collected light is blocked by the mirror and rail.

The focused light from the discrete element collector system is next sent through an aperture and collimated by a 1 inch lens with a focal length of 0.7 inch. This beam is then directed through an optical filter assembly and delivered to the PMT photodetector. The particular wavelengths are selected by changing the filter pack cap assembly on the end of the PMT assembly. Currently, three filter packs have been assembled.

Filter pack number F001 was assembled to collect 580 nm wavelength photons. It contains two 580 nm band pass interference filters followed by two 550 nm long pass absorption filters. The band pass filters are Oriel part number 54390 providing about 60% transmission at 580 nm, with a band pass of 10 nm, and 10e4 attenuation outside that band. The long pass filters are Oriel part number 51502 providing 50% transmission at 550 nm, with nearly 99% at 580 nm and 100% at 600 nm and above, and 10e5 attenuation to shorter wavelengths. The band pass filters are placed in front of the long pass filters to reduce the amount of absorption that the long pass filters may re-emit as fluorescence.

Filter pack number F002 was assembled to collect 518 nm wavelength photons. It contains one 518 nm band pass interference filter followed by one 515 long pass absorption filter. The band pass filter is Barr part number 518/8 nm providing about 60% transmission at 518 nm, with a band pass of 8 nm, and better than 10e6 attenuation outside that band. The long pass filter is an Oriel 51494 providing 50% transmission at 515 nm, about 60% at 518 nm, and 100% at 570 nm and above, and 10e5 attenuation to shorter wavelengths. Again, the band pass filter is placed in front of the long pass filter.

Filter pack number F003 was assembled to reject the 488 nm wavelength of the laser and pass longer wavelengths. It contains one long pass interference filter, Barr part number LP488nmRej. It provides 80 to 85% transmission to 515 nm and longer and better than 10e12 attenuation to 488 nm.

Neutral density filters may be used to reduce the laser beam intensity. Oriel part numbers 50550 and 50570 provide 1% and 0.01% transmission respectively. They are usually placed in a mount and inserted in the path of the laser beam as it enters the enclosure.

The Z stage was assembled using a Newport model 440-4 low profile translation stage modified to accommodate a 20 turns per inch lead screw assembly and a Superior Electric 150 oz inch stepper motor. The stepper motor gives 200 1.8 degree steps per revolution and, in half step operation, provides 3.175 microns of linear travel per step over a range of about 3 inches. With a 20 mm diameter beam incident upon the 233 mm focal length of the lens, this yields a 0.273 micron beam diameter change per step of the Z translation.

Limit switches have been positioned at the end travel points of the Z stage to prevent damage to the mechanism and to provide a means of calibrating the beam diameter. A calibration program finds where the beam comes to a focus on the sample as a function of step position from the larger beam limit switch. From this known step position, the beam diameter increases 0.273 microns per half step pulse of the stepper motor. Diameters from aperture uncertainty of 4.2 microns to about 5 mm are available. The current calibration method is providing a $+/-15$ micron uncertainty in finding the actual focal point. This error applies directly to all beam sizes.

The X-Y stage was assembled using a Newport model 405 dual-axis translation stage. It has been modified to accommodate a 20 turn per inch lead screw fabricated from ¼ inch—20 stock stainless steel threaded rod. Use of two stepper motors (the same model as for the Z stage) provides 3.175 microns of linear travel per step for both the X and Y axis. Total travel for X and Y is limited to about one half inch. Limit switches at each axis end provide a means of centering the stage. This establishes a known reference x,y of 0,0. Image scanning of the
sample can then be performed on multiples of 3.175 micron grids.

Electronics

The PMT used is the Hamamatsu 1477 one inch side on tube. The tube is constructed with a multialkali photocathode with a UV glass window and has a photon to electron gain on the order of $5.3 \times 10^6$ at an anode to cathode potential difference of 1000 volts.

The current output of the PMT is directly coupled to the pulse generator circuit. This circuit provides both a digital and analog operating mode. In the digital mode, single electronic pulses are counted as single photon events. This mode, also known as the photon counting mode, is only possible at low levels of light where photons are generally spaced far enough apart to prevent dc biasing. In the analog mode, the electronic signal is weighed proportional to the light intensity. This mode is used when there is sufficient light to permit dc biasing.

In the digital mode, the circuit converts the current from the tube into a voltage level, compares the voltage value against a preset reference value (discriminator level), and generates a pulse to the remote counter circuit. Each pulse to the counter is then counted as a single photon event. In the analog mode, the voltage level from above is integrated and used to generate a pulse frequency that is directly proportional to the voltage and consequently proportional to the incident light intensity.

A pair of operational amplifiers comprise the preamp portion of the pulse generator circuit. The preamp portion converts current pulses around a micro-ampere into a voltage pulse of approximately 1.0 volt. This signal is sent to both digital and analog portions of the circuit. A comparator is used as a discriminator to detect when these pulses are greater than a preset value in the digital portion. When the pulses are greater than the discriminating level, a logic transition occurs and a pulse shaper circuit converts this into a defined 10 nsec pulse.

In the analog portion, the voltage pulses are integrated to produce a dc voltage value. This value is transformed into a square wave frequency with a voltage-to-frequency converter. The output frequency from this converter is also shaped into 10 nsec pulses. With the selected mode of operation, the pulses are delivered to a video line driver circuit for transmission to the computer interface. The integrated voltage is also compared against a preset reference (saturation level) to determine which mode of operation is appropriate for measurement. The output of this comparator circuit is sent to the computer interface and tells the computer if the PMT counting rate is too high for the digital (photon counting) mode. The converse is that this signal also tells if the light level is too low for the analog mode. The analog or digital mode is then selected by control of a logic signal from the computer circuitry.

A means of remotely setting the discriminator level and the saturation level by computer control can be provided. This feature provides the ability to collect probability height distribution data automatically and set the discriminator level to the optimum point. The saturation level can also be determined and set by computer control. Non-volatile memory on the circuit retains the setting levels.

The computer interface consists of circuitry to convert the PC computer instructions into logical commands and status information into computer logic. This interface is built on a full size card for a PC slot. The basic components on the card are the bus transceiver, address decoders, function latches, line receiver, and counter circuits.

The computer interface uses 8 I/O port address, hex 0310 to 0317. Reads from ports 0310 to 0312 provide 20 bits from the counters. When the counters are gated by the timer circuit, with a write to 0317, pulses received by the line receiver are counted for the defined gate period. The gate period is programmed by writes to locations 0310 to 0312. Precise gate periods from 1 microsecond to 655,350 seconds are available.

The 20 bits of counts provide capability to greater than 1 million. Additional bit patterns written to ports 0313 to 0315 provide control of laser shutter, high voltage power supply, the three axis motors, and the operating mode of the timer circuit and the remote pulse generator. A read from 0313 provides information regarding the three axis limit switches.

The motor driven board accepts logic signals from the computer interface and translates them into position commands. Logic lines for each axis provide motor enable, direction, step size, and the step pulse. Limit switches at the three axis ends are delivered to the computer interface and also wired to protection circuitry. The protection circuitry prevents the stepping of the motors when the limits have been reached in the event that computer instructions fail to detect the limit.

The integrated circuits (I.C.) that control the motors are mounted on a large heat sink. Internal circuitry within the I.C.'s will shut down in the event that an excessive amount of heat should occur. The motors are Superior Electric 105 oz inch driven in an H-Bridge mode with the center taps left open.

The high voltage and laser shutter are controlled by manual on, manual off, or computer operation. The manual on position provides a means of examining the beam incident upon the sample and the capability of looking at photon counts when outside of the main data collection software package. Manual off provides the ability to never expose the sample and to insure that voltage is not present to the PMT. The high voltage control is also interlocked to prevent it from being applied when the door is open or the internal light has been left on. These interlocks prevent saturation currents within the PMT that might cause damage.

A Power One model HCC15.3A +/−15 volt power supply provides power to the circuitry for the pulse generator circuit and the high voltage portion. An adjustable regulator in the package sets the control voltage supplied to a Thorn EMI model HV1.5PN high voltage supply. A 0.0 to 10.0 volt input produces a 0.0 to 1000.0 volt output for the PMT. A Power One HB24-6A 24 volt power supply provides power to the motor circuitry and control for the laser shutter.

Two electronic circuits have been assembled to provide a means of testing and calibrating the instrument. One circuit, the gate calibrator, is packaged in a small box with an internal battery and provides a pulse output at a specified frequency as set by the front panel control. The other circuit, the LED calibrator, is packaged in a PMT cap assembly with a battery and provides a means of setting various light levels.

The gate calibrator generates frequencies from 1 Hz to 1 MHz in powers of 10. These are accurate references to test the counting software and are consequently used to calibrate the computer counter gate period. The cable is removed from the pulse generator and connected to this package to perform this test. Setting the front dial for 1 MHz should yield a count equal to the gate period in microseconds. This becomes a complete integrity test of the software, the computer and interface, the counters, and the cable.

The LED calibrator provides a means of testing the PMT and the pulse generator. Fixed intensity levels should yield a consistent count from time to time since the package is always positioned the same with respect to the PMT. The circuit contains very stable references and regulators to maintain constant current to the LED and, the LED is mounted in a small metal casting that is temperature regulated. Temperature variations of the LED junction have shown variations in emitted light. This test is also very useful in verifying the performance of the electronics and software mathematical operations by monitoring the counting statistics, i.e., the standard deviation divided by the square root of the mean.

Computer

A PC compatible computer is used to control the instrument, make the measurements, and perform the analysis and imaging. A printer and color plotter are attached for hard copy outputs.

The computer motherboard is equipped with an Intel 80286 microprocessor, an 80287 math coprocessor, 1024 Kbyte memory, keyboard and speaker connections, and 8 expansion slots.

An AST Advantage multifunction board provides 576 Kbytes of extended memory, one serial port for the plotter, and one parallel port for the printer. An IBM hard/floppy disk controller board and external floppy disk driver board provide communication links to the storage media. A Video Seven VEGA VGA board provides high resolution graphic capability up to 800×600 pixels.

Of the three board slots remaining, one is used by a custom developed circuit card for control and monitoring of the instrument and two slots are available for expansion. The custom board is the computer interface board discussed in the electronic section. It provides the means of controlling the instrument data collection.

Software

The data collection software is the program AML-M.EXE, written in the C programming language. It was compiled with the Microsoft C compiler version 5.1 and linked with libraries from Microsoft and Vermont Creative Software. It is a window oriented package with several levels for data collection and maintenance operations. Data files written to the 3.5 inch drive include a binary .FCD file containing header information, operating parameters, and the data. Also written, dependent upon the mode of operation, are .GRD files for 3-D image plotting, .DAT files containing X and Y coordinates and photon count data, and .COR files with just coordinates.

The .DAT file can be used to provide a .GRD file that uses smoothing factors for interpolation of missing data points. The .COR file can be used to re-image at the same locations as a previous run.

The analysis software is the program PVAL.EXE, also written in C. It is also a windowing package that gives information about the data collected, such as the mean value and standard deviation. The program gets the data from the .FCD file.

The graphic software is the program GRAPH.EXE, written in C and linked with the GSS Graphic libraries. This provides a visual display of the data collected and capability of sending the display to the color plotter. This program also gets the data from the .FCD file.

The Golden Surfer package is a commercial product that does the 3-D surface imaging and 2-D topographical views. There are six programs, GRID, SURF, TOPO, VIEW, PLOTCALL, and PLOT. GRID reads data files containing X, Y, and Z data and provides the means to generate a grid image of the data. The output from this program can be read by SURF for 3-D imaging or by TOPO for 2-D contours. PLOTCALL and PLOT provide the means to output these views to the color plotter. VIEW is a utility that displays the plotter generated files on the screen and provides zoom and pan functions.

The Lotus 123 spreadsheet software package is also used in analysis of data. Data that is not normally collected automatically by the instrument can be processed and displayed by the graphic functions. Other scientific processing can also be applied to data collected by the instrument, such as applying photon pulse pile up correlation equations to the actual data.

Figure 5:
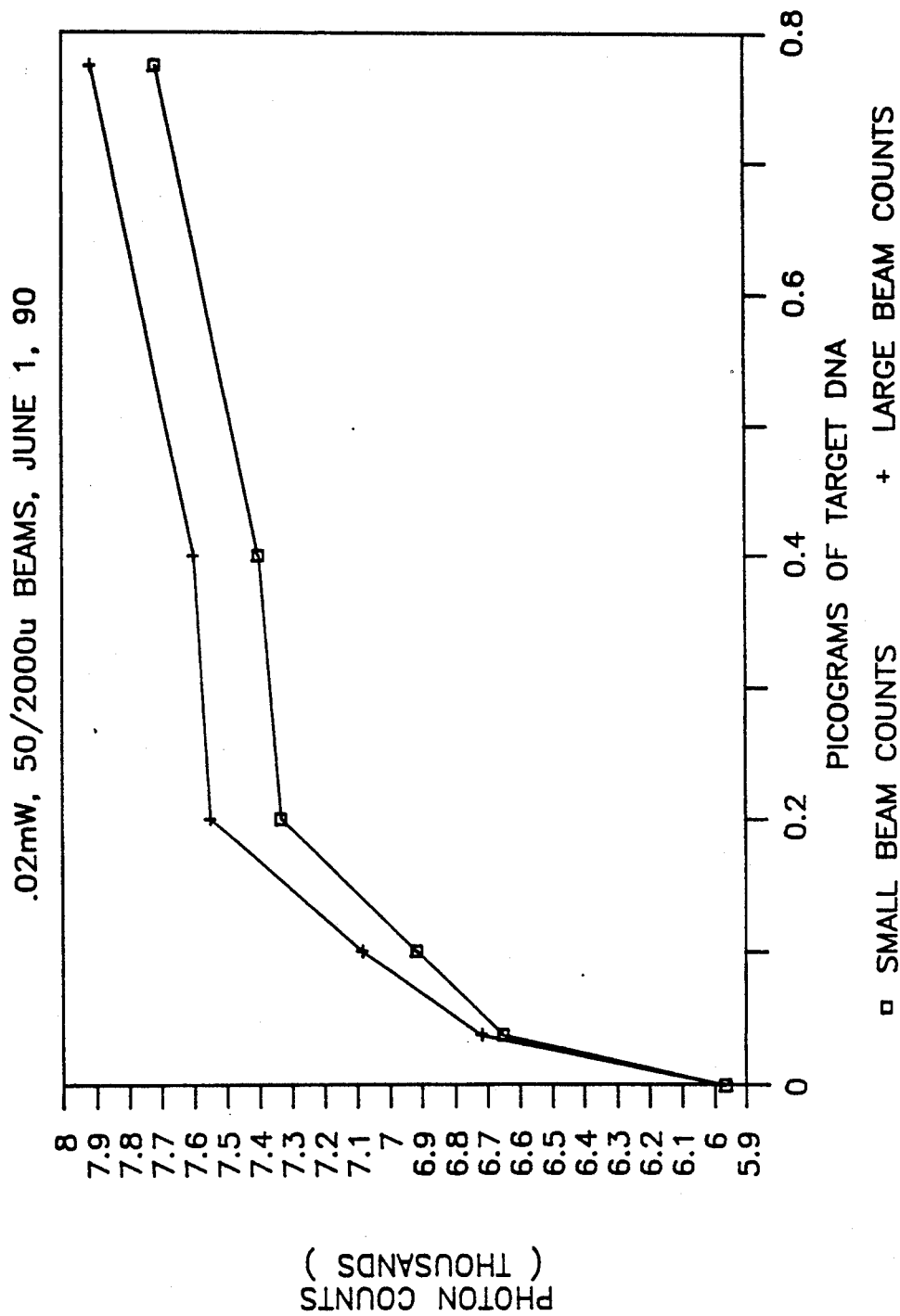
FIG. 5 is a graph of the result obtained with varying levels of picograms of target DNA stained with a fluorescent dye.

FIG. 5 shows a plot of the data with the number of fluorescent counts per sample for several different samples with increasing content of sample DNA (from 0.05 to 0.8 picograms DNA per sample). The data was obtained a follows: biotinylated DNA standard (lambda digest) was purchased from Vector Labs (Burlingame, Calif.). The biotinylated DNA was serially diluted (by factors of two) in a 6× SSC buffer (1× SSC buffer is 0.15M NaCl, 0.015M NaCitrate, pH 7.0) containing 100 pg/ul of salmon sperm DNA (Sigma Chemical Co., St. Louis, Mo.).

Nitrocellulose membrane (0.45 um, cat. #20460, Schleicher and Schuell, Keene, N.H.) was pretreated by first wetting in dH$_2$O, then soaking the membrane for 20 minutes in 20× SSC with gentle agitation. The filters were then air dried.

Two microliters of each of the appropriate DNA dilutions were spotted onto the designated area of the pretreated filter membrane (1 mm diameter spots) and allowed to dry. The DNA was crosslinked onto the nitrocellulose by exposure to bright white lights (General Electric Sunlamp 275 W, 110 V, Vector Labs, Burlingame, Calif.) at a distance of 10 cm for 5 minutes.

The filter was washed in 3 changes of TTBS (TTBS is 0.1M Tris-HCl, 0.15M NcCl, 0.1% Tween-20, pH 7.5) over 30 minutes with agitation.

Fluorescein-conjugated avidin DN (cat. #A-3101, Vector Labs, Burlingame, Calif.) was diluted 1:50 in TTBS. The filters were incubate in the TTBS containing fluorescein conjugated avidin DN for 30 minutes in the dark. The filters were then washed in 3 changes of TTBS over 30 minutes with agitation.

Biotinylated anti-avidin D from goat, affinity purified (cat. #BA-0300, Vector Labs, Burlingame, Calif.) was diluted 1:50 in TTBS. The filters were incubated in the TTBS containing the biotinylated anti-avidin D for 30 minutes in the dark. After incubation, the filters were washed with 3 changes of TTBS as before.

The filters were then incubated again in fluorescein-conjugated avidin DN in TTBS for 30 minutes in the dark and washed as previously described. The double-stained filters were allowed to air dry in the dark.

The fluorescent spots were then scanned in the sensitive light detection system as described in FIG. 1. The laser power was 0.02 mW and the beam diameter was focussed to 50 um. The photon counts per spot as a function of mass of biotinylated DNA in the spot is shown in FIG. 5.

It is evident from the above results and the description of the device, that accurate determinations can be made at low levels of analyte using fluorescence or other label providing for emitted light. In this way, one may detect a wide variety of analytes which may be present at only extremely low concentrations. In addition, because one allows for movement of the sample in relation to the light irradiation and collection system, one may provide for a variety of measurements of different analytes, by having different complementary members at different sites on a surface. The lens system allows for variation of the size of the beam, while the system allows for movement of the sample, so that different areas of the sample may be interrogated. The high collection efficiency of the Fresnel lens system allows for detection of extremely low levels of light, where discrimination can be made between different intensities.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An improved sensitivity light collection system capable of detecting luminescence from emitters in biological assay media comprising a sample resulting in a very low signal level, said light detection system comprising:

means for collecting emitted light from said assay media comprising a discrete element collector system, said system having a first discrete element collector catadioptric lens proximal to said sample having a small focal length and a low f number in the range of about 0.05-2 for collecting and collimating emitted light; and a second lens in light receiving relationship when said first discrete element collector separated by from about 0.1 to 50 cm from said first discrete element collector and distal from said sample having a greater focal length and a larger f number in the range of about 1-10 for focusing said collimated emitted light collected by said first discrete element collector; and photodetecting means for detecting light transmitted by said discrete element collector system.

2. A light detection system according to claim 1, including an irradiation source for directing a beam onto said sample, wherein said beam passes through a hole in said discrete element collector system.

3. A light detection system according to claim 1, wherein said first discrete element collector has an f-number in the range of about 0.075-1 and said second lens has an f-number of greater than about 1.

4. A light detection system according to claim 1, wherein said second discrete element collector lens is a Fresnel lens.

5. A light detection system for detecting light transmitted from a surface at a very low signal level as a result of light irradiation, said light detection system comprising:

means for providing a beam of light for irradiating a surface or volume with a beam of defined wave length range;

means for collecting emitted light from said surface or volume comprising a discrete element collector system, said system having a first discrete element collector catadioptric lens proximal to said sample having a small focal length and a low f number in the range of about 0.075-1 for collection and collimating emitted light; and a second lens in light receiving relationship with said first discrete element collector lens separately by from about 0.1 to 5 cm from said first discrete element collector and distal from said sample having a greater focal length and a larger f number in the range of about 1-10 for focusing said collimated emitted light collected by said first discrete element collector lens, wherein said beam irradiates said surface without interacting with said discrete element collector system; and photodetecting means for detecting light transmitted by said discrete element collector system.

6. A light detection system according to claim 5, wherein said beam passes through a hole in said discrete element collector system.

7. A light detection system according to claim 5, wherein said light source is a laser having a wavelength in the range of about 350 to 700 nm.

8. An emitted light detection system for detecting an analyte in a sample, said decision system comprising:

a sample support;

means for providing a beam of light for irradiating a sample on said sample support with a beam of defined wave length range;

means for controlling the area of said beam impinging on said sample;

means for moving said sample support and beam relative to one another;

means for collecting emitted light from said sample comprising a discrete element collector system, said system having a first discrete element collector catadioptric lens proximal to said sample having a small focal length and a low f number in the range of about 0.075-1 for collecting and collimating said emitted light; and a second lens in light receiving relationship to said first discrete element collector lens separately by from about 0.1 to 5 cm from said first discrete element collector and distal from said sample having a greater focal length and a larger f number in the range of about 1-10 for focusing said emitted light collimated by said first discrete element collector lens;

means for filtering emitted light to isolate enough sample emission from excitation wavelength;

photodetecting means for detecting light transmitted by said discrete element collector system; and means connected to said photodetecting means for relating a signal from said photodetecting means to the presence of analyte in said sample.

9. A device according to claim 8, wherein said light source is a laser having a wave length in the range of about 350 to 700 nm.

10. A device according to claim 8, wherein said sample support is at least partially transparent; and further comprising:

a reflector below said sample support for transmitting light to said discrete element collector system.

11. A device according to claim 8, wherein said device further comprises a movable stage supporting said sample support.

12. A device according to claim 8, wherein said beam area controlling means includes means for varying the beam size.

13. An emitted light detection system for detecting an analyte in a sample, said detection system comprising:

a sample support on a movable stage;

a laser light source for irradiating a sample on said sample support with a beam of defined wavelength range;

means for controlling the area of said beam impinging on said sample;

means for moving said sample support and beam relative to one another;

means for collecting emitted light from said sample comprising a discrete element collector system, said system having a first discrete element collector catadioptric lens proximal to said sample having a small focal length and a low f number in the range of about 0.075–1 for collecting and collimating said emitted light; and a second lens in light receiving relationship with said first discrete element collector lens separated by from about 0.1 to 5 cm from said first discrete element collector and distal from said sample having a greater focal length and a larger f number in the range of about 1–10 for focusing said collimated light collected by said first discrete element collector lens, wherein said beam does not interact with said discrete element collector system;

means for filtering emitted light to isolate sample emission from excitation wavelength;

photodetecting means for detecting light transmitted by said discrete element collector system; and means connected to said photodetecting means for relating a signal from said photodetecting means to the presence of analyte in said sample.

14. A device according to claim 13, wherein said area controlling means comprises a single or multi-lens system and said second lens is a Fresnel lens.

15. A device according to claim 13, wherein said sample is irradiated at an angle normal to said sample and the irradiating light passes through a hole in said discrete element collector system.

16. A device according to claim 13, wherein said sample is irradiated at an angle at other than normal to said sample and the irradiating light.

17. A device according to claim 13, wherein said sample support is at least partially transparent; and further comprising:

a reflector below said sample for transmitting light to said discrete element collector system.

18. A method for detecting low levels of emitted light from a sample, said method comprising:

activating a sample suspected of being capable of emitting light upon activation;

collecting light from said sample with a discrete element collector system, said collector system having a first discrete element collector catadioptric lens proximal to said sample having a small focal length and a low f number in the range of about 0.05–2 for collecting and collimating emitter light; and a second lens in light receiving relationship to said first discrete element collector lens separated by from about 0 to 50 cm from said first discrete element collector and distal from said sample having a greater focal length and a larger f number in the range of about 1–10 focusing said collimated emitted light collected by said first discrete element collector;

detecting light transmitted by said discrete element collector system, wherein the level of light detected is related to the level of light emitters in said sample.

19. A method according to claim 18, wherein said irradiating is at different portions of said sample and said detecting is as to each of said portions of said sample.

20. A method according to claim 18, wherein said first discrete element collector lens is a catadioptric lens, said lens having a f-number in the range of about 0.075–1.

21. A method according to claim 18, wherein said activation is irradiation and said activating comprises irradiating said sample with light at an excitation wavelength range.

* * * * *